(12) United States Patent
Vidal et al.

(10) Patent No.: US 9,284,262 B2
(45) Date of Patent: Mar. 15, 2016

(54) PROCESS FOR PREPARING ESTERAMIDE COMPOUNDS

(75) Inventors: Thierry Vidal, Lyons (FR); Rabih Rached, Millery (FR); Massimo Guglieri, Anhangabau-Jundiai (SP) (BR)

(73) Assignee: RHODIA OPERATIONS, Aubervilliers (FR)

( * ) Notice: Subject to any disclaimer, the term of this patent is extended or adjusted under 35 U.S.C. 154(b) by 335 days.

(21) Appl. No.: 13/702,470

(22) PCT Filed: Jun. 9, 2011

(86) PCT No.: PCT/FR2011/051315
§ 371 (c)(1),
(2), (4) Date: May 14, 2013

(87) PCT Pub. No.: WO2011/154661
PCT Pub. Date: Dec. 15, 2011

(65) Prior Publication Data
US 2013/0237722 A1    Sep. 12, 2013

(30) Foreign Application Priority Data
Jun. 9, 2010 (FR) .................... 10 54534

(51) Int. Cl.
*C07C 231/02* (2006.01)
*C07C 231/14* (2006.01)

(52) U.S. Cl.
CPC ............. *C07C 231/14* (2013.01); *C07C 231/02* (2013.01)

(58) Field of Classification Search
CPC .......................... C07C 231/02; C07C 231/14
See application file for complete search history.

(56) References Cited

U.S. PATENT DOCUMENTS

| | | | |
|---|---|---|---|
| 3,288,794 | A | 11/1966 | Kuceski |
| 3,417,114 | A | 12/1968 | Kuceski |
| 4,588,833 | A | 5/1986 | Kadelka et al. |
| 2011/0166025 | A1 | 7/2011 | Jentzer et al. |

OTHER PUBLICATIONS

Zradni et al., "Synthesis of Amides from Esters and Amines Under Microwave Irradiation," Synthetic Communications, 32(22), 3525-3531, 2002.*
Moon, "Synthesis and Acylation of Pyrrolinones," J. Org. Chem., 42(13), 2219-2223, 1977.*
ICSC Database Card, http://www.ilo.org/dyn/icsc/showcard.display?p_lang=en&p_card_id=1483, accessed Feb. 5, 2015 (Feb. 2009).*
International Search Report for PCT/FR2011/051315 dated Sep. 28, 2011.
International Preliminary Report on Patentability for PCT/FR2011/051315 dated Dec. 10, 2012.

* cited by examiner

*Primary Examiner* — Paul A Zucker
*Assistant Examiner* — Mark Luderer
(74) *Attorney, Agent, or Firm* — B. Aaron Schulman, Esq.; Stites & Harbison, PLLC

(57) ABSTRACT

The present invention relates to a method for preparing esteramide compounds. More particularly, the invention relates to a method for preparing esteramide compounds by reaction between a diester and an amine, in the presence of a basic compound, wherein
- the amine is solubilized in an organic solvent or in the diester,
- when the amine is solubilized in an organic solvent, the diester is added onto the reaction mixture comprising the amine and the basic compound,
- when the amine is solubilized in the diester, the basic compound is added onto the reaction mixture comprising the amine and the diester (II),
- the reaction is conducted at a temperature greater than or equal to 30° C.,
- the amine is present in molar excess ranging from 0.01 to 50% relatively to the diester.

14 Claims, No Drawings

PROCESS FOR PREPARING ESTERAMIDE COMPOUNDS

The present invention relates to a method for preparing esteramide compounds.

More particularly, the invention relates to a method for preparing esteramide compounds by reaction between a diester and an amine.

Esteramide compounds are known for their applications as solvents, notably in plant protection applications, as described for example in document WO 2009/092795.

There exist several routes for accessing said esteramide compounds.

Document U.S. Pat. No. 4,588,833 describes a method for preparing an esteramide by a high temperature reaction, catalyzed by cobalt, of an unsaturated amide with an alcohol and carbon monoxide.

Document U.S. Pat. No. 3,417,114 describes in Example 9, a method for simultaneous preparation of an esteramide compound <<DMGME>> of formula: MeOOC—$(CH_2)_3$—$CONMe_2$ and of a diamide compound <<TMG>> of formula: $Me_2NOC$—$(CH_2)_3$—$CONMe_2$, followed by separation of both of these compounds by distillation. In order to conduct the reaction, gaseous dimethylamine is bubbled for two hours in a medium comprising dimethyl glutarate purified beforehand and a solution of sodium methylate. Both compounds (DMGE and TMG) aren't then isolated by distillation from the obtained complex mixture.

Document U.S. Pat. No. 3,288,794 describes the same method as document U.S. Pat. No. 3,417,114 as well as the simultaneous preparation of N,N-dimethyl-adipamide methyl ester and N,N,N',N'-tetramethyl-adipamide methyl ester with a similar operating procedure, also followed by separation by distillation.

In the case of diesters, the methods of the prior art, described above are not selective for esteramide. The proportion of diamide is moreover, often a majority proportion and the esteramide is considered as a byproduct which has not totally reacted.

Further, for such sure methods, a step for purifying the diester prior to the reaction is required, which complicates the method.

This type of method also requires unwieldy and costly treatments of the reaction medium after reaction in order to isolate the diamide and the esteramide, such as for example distillations.

Further, with these methods of the prior art, the formed raw products may have a strong yellow-orangey coloration which is a nuisance for subsequent uses. The products are therefore subject to additional purification steps. All these purification treatments complexify the methods for making esteramides.

In order to attempt to overcome the problem of low esteramide selectivity, it is common to operate at low temperatures, i.e. below room temperature, by cooling the reaction medium. However, lowering the reaction temperature, significantly reduces the kinetics of the reaction and therefore the productivity of the method.

Therefore, there exists a need for finding a method for making esteramide compounds from diesters which is selective for esteramide. Further, the method should be easy to apply in an industrial installation. Another requirement which the method has to meet, is that the kinetics of the reaction should be large. Finally, the method for making esteramide should be productive.

For this purpose, the present invention proposes a method for preparing an esteramide compound of the following formula (I):

$$R^1OOC\text{-}A\text{-}CONR^2R^3 \qquad (I)$$

comprising a reaction step between:
a diester compound of the following formula (II):

$$R^1OOC\text{-}A\text{-}COOR^1 \qquad (II)$$

and an amine of the following formula (III):

$$HNR^2R^3 \qquad (III)$$

in the presence of a basic compound,
wherein:
A is a covalent bond or a linear or branched divalent alkylene group comprising a number of carbon atoms ranging from 1 to 12,
$R^1$ is an optionally substituted hydrocarbon group comprising from 1 to 36 carbon atoms,
$R^2$ and $R^3$, either identical or different, are groups selected from a hydrogen atom and optionally substituted hydrocarbon groups, comprising from 1 to 36 carbon atoms,
$R^2$ and $R^3$ may form together a ring comprising the nitrogen atom to which they are bound, said ring being, if necessary, substituted and/or comprising an additional heteroatom, and
$R^2$ and $R^3$ not being simultaneously hydrogen atoms,
characterized by the fact that
the amine (III) is solubilized in an organic solvent, or in the diester compound (II),
when the amine (III) is solubilized in an organic solvent, the diester compound (II) is added on to the reaction mixture comprising the amine (III) and the basic compound,
when the amine (III) is solubilized in the diester compound (II), the basic compound is added onto the reaction mixture comprising the amine (III) and the diester compound (II),
the reaction is conducted at a temperature greater than or equal to 30° C.,
the amine (III) is present in molar excess ranging from 0.01 to 50%, based on the diester compound (II).

According to the method of the invention, the amine (III) is always present in the reaction medium onto which one of the compounds (diester or basic compound) is added, the other compound (basic or diester compound), being present with the amine from the onset of the reaction.

A diester compound of formula (II) is therefore involved in the method of the invention, which compound advantageously has the characteristics below.

According to an advantageous embodiment of the invention, in the formulae (I) and (II), A is a branched divalent alkylene group comprising a number of carbon atoms ranging from 2 to 12, preferably ranging from 3 to 6 carbon atoms.

Preferably, in the formulae (I) and (II), the groups $R^1$, either identical or different, are hydrocarbon groups, comprising from 1 to 16 carbon atoms, and may bear one or several substituents. By <<substituent>>, is meant, as an illustration and with no limitation, an alkyl group, preferably having from 1 to 4 carbon atoms, alkoxy group preferably having from 1 to 4 carbon atoms, hydroxy or halogeno group.

Preferentially, the groups $R^1$, either identical or different, are selected from alkyl, alkenyl, cycloalkyl, aryl and arylalkyl groups, said groups may bear one or several substituents.

More particularly, $R^1$ is preferentially selected from methyl, ethyl, n-propyl, isopropyl, n-butyl, isobutyl, tertiobutyl, sec-butyl, n-pentyl, isopentyl, sec-pentyl, cyclopentyl, n-hexyl, isohexyl, sec-hexyl, cyclohexyl, methylcyclohexyl, 2-ethylbutyl, 3-methylpentyl, n-heptyl, isoheptyl, sec-heptyl, 3-methylhexyl, 4-methylhexyl, 1-ethylpentyl, 2-ethylpentyl, 3-ethylpentyl, n-octyl, isooctyl, 3-methylheptyl, n-nonyl, n-decyl, undecyl, n-dodecyl, tridecyl, tetradecyl and pentadecyl groups.

In a particularly advantageous embodiment, $R^1$ is selected from methyl and ethyl groups.

Most preferentially, the diester compound of formula (II) is a mixture of diester compounds of the following formulae (II.1), (II.2) and (II.3):

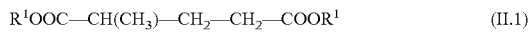  (II.1)

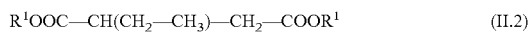  (II.2)

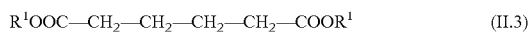  (II.3)

with $R^1$, as defined above.

The mixture of diester compounds of formula (II.1), (II.2) and (II.3) may have the following composition:
- from 75 to 95% by weight of compound of formula (II.1), preferably from 85 to 95% by weight,
- from 3 to 23% by weight of compound of formula (II.2), preferably from 4 to 14% by weight,
- from 0.1 to 10% by weight of compound of formula (II.3), preferably from 0.1 to 3% by weight.

It is more preferred that for the mixture of diester compounds of formula (II.1), (II.2) and (II.3) above, the groups $R^1$ be methyl groups. This may notably be a mixture of diesters marketed by Rhodia under the name of Rhodiasolv® IRIS.

According to an advantageous embodiment of the invention, the diester compound (II) is introduced as pure, i.e. it is not put into solution in an organic solvent. However, it is possible that the diester compound (II) be put into solution in an organic solvent. According to a preferred embodiment of the invention, the organic solvent is selected from volatile organic solvents, notably alcohols and ethers, preferably from methanol, ethanol, tetrahydrofurane (THF), and mixtures thereof. More preferentially, the organic solvent is methanol.

An amine of formula (III) is also involved in the method of the invention, which amine advantageously has the characteristics below.

Preferably, in the formulae (I) and (III), the groups $R^2$ and $R^3$, either identical or different, are hydrocarbon groups, comprising from 1 to 16 carbon atoms, which may bear one or several substituents. By <<substituent>> is meant, as an illustration and not as a limitation, an alkyl group preferably having from 1 to 4 carbon atoms, an alkoxy group preferably having from 1 to 4 carbon atoms, a hydroxy or halogeno group.

Preferentially, the groups $R^2$ and $R^3$, either identical or different, are selected from alkyl, alkenyl, cycloalkyl, aryl and arylalkyl groups, said groups may bear one or several substituents.

According to a first embodiment of the invention, $R^2$ and $R^3$, either identical or different, are selected from methyl, ethyl, hydroxyethyl, n-propyl, isopropyl, n-butyl, isobutyl, tertiobutyl, n-pentyl, isoamyl, hexyl and cyclohexyl groups. Preferably, $R^2$ and $R^3$ are selected from methyl, ethyl and hydroxyethyl groups.

According to a second embodiment of the invention, $R^2$ and $R^3$ form together a ring of 5 or 6 atoms comprising the nitrogen atom to which they are bound, one of the ring atoms may be another heteroatom, such as for example an oxygen atom. Preferably, $R^2$ and $R^3$ form together a ring selected from a morpholine, piperidine and piperazine ring.

The amine of formula (III) is solubilized in an organic solvent, or in the diester compound (II).

According to a preferred embodiment of the invention, the organic solvent is selected from volatile organic solvents, notably alcohols and ethers, preferably from methanol, ethanol, tetrahydrofurane (THF), and mixtures thereof. More preferentially, the organic solvent is methanol.

The amine of formula (III) is present in a weight concentration in the organic solvent which is advantageously comprised between 10 and 100%, preferably between 30 and 80% and still more preferentially between 40 and 60%. The case when the amine (III) is present in a 100% concentration corresponds to the embodiment in which the amine is solubilized in the diester compound (II), and when there is no additional organic solvent.

The method of the invention applies a basic compound.

Preferably, the basic compound is an alkaline or earth alkaline metal alkoxide preferably selected from sodium methylate, sodium or potassium ethylate, potassium tertbutylate. The basic compound may also be selected from carbonates, notably potassium or sodium carbonate; or alkyl titanates such as for example butyl titanate. The basic compound may also be a mixture of several compounds mentioned above. Preferably, the basic compound is sodium methylate.

According to the invention, the basic compound may be used either pure or in solution in an organic solvent, for example with a same nature as the one defined earlier, notably methanol. Generally, the basic compound is in solution in an organic solvent at a weight concentration in the organic solvent, which is advantageously comprised between 5 and 80%, preferably between 10 and 50% and still more preferentially between 20 and 30%.

According to the invention, the diester compound of formula (II) and the amine of formula (III) are reacted in the presence of the basic compound, in the proportions defined hereafter.

According to a feature of the invention, the amine (III) is present in molar excess ranging from 0.01 to 50%, based on the diester compound (II). Preferably, the amine is present in molar excess ranging from 1 to 30% and still more preferentially from 5 to 20%, based on a diester compound (II). The stoichiometry for obtaining the esteramide compound of formula (I) being of 1 mole of amine of formula (III) per mole of diester compound of formula (II), by "molar excess" is meant here that the method of the invention involves a molar excess of amine ranging from 0.01 to 50% based on this stoichiometric amount.

The basic compound is preferably introduced at a molar concentration relatively to the diester comprised between 0.01 and 20%, preferably between 3 and 10%.

According to another feature of the invention, the reaction is conducted at a temperature greater than or equal to 30° C. Preferably, the reaction is conducted at a temperature greater than or equal to 50° C. Advantageously, the reaction is conducted at a temperature comprised between 30° C. and 130° C., preferably between 40° C. and 90° C. and even more preferentially between 45° C. and 65° C. The calories required for controlling this temperature are either provided by the reaction itself or by an external means, for example by heating or cooling.

Advantageously, the reaction is conducted at a pressure comprised between 1 and 10 bars absolute, preferably between 1 and 5 bars absolute and even more preferentially between 1 and 3 bars absolute.

Preferably, the reaction is conducted under anhydrous conditions; i.e. up to 0.2% by weight of water, preferably up to 0.05% by weight of water are tolerated.

According to a preferred embodiment, the reaction is conducted under inert conditions, for example by sweeping with an inert gas, notably nitrogen.

According to the invention, the (diester or basic) compound which is added onto the reaction mixture comprising the amine (III) may be added in one go, continuously or portionwise.

According to the invention, at the end of the reaction, the esteramide compound of formula (I) is obtained. The reaction mixture at the end of the reaction does not require any unwieldy purification treatment of the esteramide compound for separating it from the diamide compound. Only the volatile compounds like the unreacted amine and the solvent may be removed, notably evaporated, for example by distillation under reduced pressure. The medium may optionally be treated with conventional operations known to one skilled in the art, notably neutralization, filtration and washing steps for removing the salts formed during the reaction. The thereby obtained esteramide compound of formula (I) has high purity and may be directly used in applications for which it is intended, for example as a solvent, notably in plant protection applications.

The method according to the invention may be a continuous or discontinuous process.

The method according to the invention has many advantages, it is most particularly advantageous when it is applied on a mixture of diester compounds fitting the formulae (II.1), (II.2) and (II.3), for example Rhodiasolv®IRIS, in the presence of a molar excess of amine (III) based on the diester mixture and at a temperature above 30° C.

First of all, it is very selective for esteramide, i.e. the esteramide selectivity is greater than 90%, or even greater than 95%. Surprisingly, less than 5% of diamide are formed in spite of the excess of amine and a reaction temperature greater than or equal to 30° C. The reaction is also very fast as compared with reactions at a lower temperature and without excess of amine. Further, no significant coloration of the medium is observed and the reaction mixture at the end of the reaction does not require any unwieldy purification treatment of the majority product, which considerably simplifies the method and increases its productivity.

The examples which follow illustrate the invention without however limiting it.

EXAMPLES

Example 1 (Comparative)

Dimethylamine (Gas) on a Rhodiasolv® IRIS/sodium methylate Mixture—T=20° C.

In a perfectly stirred 1 L double jacket reactor, provided with mechanical stirring and dried beforehand, are placed a solution of sodium methylate in methanol (a 50% by weight solution: weight, 18.8 g) and 304 g of a mixture of 2-methyl-glutaric acid, 2-ethyl-succinic acid and adipic acid diesters marketed under the name of Rhodiasolv® IRIS by Rhodia.

It is seen that the reaction medium has a yellow-orange color.

The temperature of the reaction mixture is stabilized to the set value of +20° C. and the dimethylamine gas is bubbled for two hours in the reaction medium comprising the sodium methylate and the mixture of diesters (addition of 82 g of dimethylamine, molar excess of 5% relatively to the diester).

The temperature of the reaction medium is maintained constant during the bubbling period.

The temperature of the reaction medium is maintained to +20° C. until 96% of the initially introduced diester has been consumed (completion time: 20 hours).

The slight excess of dimethylamine is distilled under reduced pressure (~200 mbars) at a temperature comprised between 20 and 50° C. The reaction medium is then neutralized by adding the sufficient amount of 85% phosphoric acid. The salts formed are filtered. The solid formed is washed with methanol and then the volatile compounds (methanol and unreacted diester) are distilled in vacuo.

The product is then analyzed by gas chromatography.

Table 1 hereafter gathers the conditions and results of this Comparative Example 1C.

TABLE 1

| Test | T (° C.) | Duration (h) [a] | Esteramide (%) [b] | Diamide (%) [b] | Di/EA [c] | Coloration of the raw reaction medium |
|---|---|---|---|---|---|---|
| 1C | 20 | 20 | 95 | 3 | 3.1 | Yellow-orange coloured |

[a] Duration required for completing the reaction
[b] Composition in this case, mentioned at the end of the treatment
[c] Di/EA = ratio of the final diamide/esteramide concentrations It is seen that the reaction is slow and that the obtained product is colored.

Example 2

Sodium Methylate on Rhodiasolv® IRIS/Dimethylamine—Mixture—Influence of Temperature In a perfectly stirred 1 L double jacket reactor, provided with mechanical stirring and dried beforehand, dimethylamine is introduced (pure DMA, 83 g, 5% molar excess relatively to the diester) solubilized in 304 g of a mixture of the diesters of 2-methyl-glutaric acid, 2-ethyl-succinic acid and adipic acid, marketed under the name of Rhodiasolv® IRIS by Rhodia.

The temperature of the reaction medium is stabilized to the desired set value (cf. Table 2 below) and a sodium methylate solution in methanol (50% by weight solution: weight 18.8 g) is poured onto the reaction mixture comprising the dimethylamine and the mixture of diesters within a defined period of time.

Once pouring is completed, the temperature of the reaction medium is maintained constant until more than 96% of the engaged diester load has been consumed.

The dimethylamine excess is distilled under reduced pressure (~200 mbars) at a temperature comprised between 20 and 50° C. The reaction medium is then neutralized by adding the sufficient amount of 85% phosphoric acid. The salts formed are filtered. The residual solid is washed with methanol and then the volatile compounds are distilled in vacuo.

The product is then analyzed by gas chromatography.

Table 2 below gathers the conditions and results of both tests applied (test 2C: comparative and test 2: according to the invention).

TABLE 2

| Test | DMA (% mol) | T (° C.) | Duration (h) [a] | Esteramide (%) [b] | Diamide (%) [b] | Di/EA (%) [c] |
|---|---|---|---|---|---|---|
| 2C | 100 | 20 | 8 | 95.8 | 4 | 4.2 |
| 2 | 100 | 50 | 1 | 96 | 4.2 | 4.4 |

[a] Duration required for completing the reaction
[b] Composition in this case, mentioned at the end of the treatment
[c] Di/EA = ratio of the final diamide/esteramide concentrations It is seen that the reaction is slow for the Comparative Example 2C while it is very fast for Example 2 according to the invention in which the selectivity is retained in spite of the increase of the temperature to a value of 50° C.

Example 3

Rhodiasolv® IRIS on a sodium methylate/dimethylamine Mixture—Influence of Temperature—Influence of DMA Excess The dimethylamine in methanol (a 50% by weight solution: weight, 188 g) and sodium methylate in methanol (50% by weight solution: weight 18.8 g) are introduced in a perfectly stirred 1 L double jacket reactor, provided with mechanical stirring and dried beforehand.

The temperature of the reaction medium is stabilized to the desired said value and 304 g of a mixture of diesters of 2-methyl-glutaric acid, 2-ethyl-succinic acid and adipic acid, marketed under the name of Rhodiasolv® IRIS by Rhodia are poured onto the reaction mixture comprising the dimethylamine and the sodium methylate within a defined period of time.

Once the pouring is completed, the temperature of the reaction medium is maintained constant until more than 96% of the engaged diester load has been consumed.

The dimethylamine excess is distilled under reduced pressure (~200 mbars) at a temperature comprised between 20 and 50° C. The reaction medium is then neutralized by adding the sufficient amount of 85% phosphoric acid. The salts formed are filtered. The residual solid is washed with methanol and the volatile compounds are then distilled in vacuo.

The product is then analyzed by gas chromatography.

Tables 3 and 4 below gather the conditions and results of the different tests applied (C corresponds to a comparative test).

Effect of Temperature
Diester/DMA/MeONa=1 mol/1.2 mol/0.05 mol—DMA at 50% by weight in methanol.

TABLE 3

| Test | T (° C.) | Duration (h) [a] | Esteramide (%) [b] | Diamide (%) [b] | Di/EA (%) [c] |
|------|----------|------------------|---------------------|-----------------|---------------|
| 3.1C | 15 | 20 | 96 | 4 | 4.2 |
| 3.2C | 20 | 12 | 95.8 | 4.2 | 4.4 |
| 3.3  | 40 | 6  | 96.2 | 3.8 | 3.9 |
| 3.4  | 50 | 3  | 95.5 | 4.5 | 4.7 |

[a] Duration required for completing the reaction
[b] Composition in this case, mentioned at the end of the treatment
[c] Di/EA = ratio of the final diamide/esteramide concentrations It is seen that the reaction rate is considerably reduced from 40° C. onwards, while retaining the esteramide selectivity.

Effect of DME Stoichiometry
Diester/MeONa=1 mol/0.05 mol—DMA at 50% by Weight in Methanol

TABLE 4

| Test | DMA (%) [c] | T (° C.) | Duration (h) [a] | Esteramide (%) [b] | Diamide (%) [b] | Di/EA (%) [d] | Comment |
|------|-------------|----------|------------------|---------------------|-----------------|---------------|---------|
| 3.5C | 0 | 20 | >24 | 96.9 | 3 | 3 | Conversion < 96% after 24 hours |
| 3.6  | 0 | 50 | >24 | 96 | 3.7 | 3.8 | Conversion < 96% after 24 hours |
| 3.7C | 10 | 20 | >24 | 96.5 | 3 | 3.1 | Conversion < 96% after 24 hours |
| 3.8  | 10 | 50 | 7.5 | 96 | 4.8 | 5 | |
| 3.2C | 20 | 20 | 12 | 95.8 | 4.2 | 4.4 | |
| 3.4  | 20 | 50 | 3 | 95.5 | 4.5 | 4.7 | |

[a] Duration required for completing the reaction
[b] Composition in this case, mentioned at the end of the treatment
[c] Molar excess of DMA relatively to the diester (mol %)
[d] Di/EA = ratio of the final diamide/esteramide concentrations It is seen that without DMA excess, the reaction is very slow. DMA excess surprisingly gives the possibility of retaining esteramide selectivity at a temperature of 50° C. Such a temperature of 50° C. further promotes kinetics of the reaction.

The invention claimed is:

1. A method for preparing an esteramide compound of the following formula (I):

$$R^1OOC\text{-}A\text{-}CONR^2R^3 \quad (I)$$

comprising a step for reaction between:
a diester compound of the following formula (II):

$$R^1OOC\text{-}A\text{-}COOR^1 \quad (II)$$

and an amine of the following formula (III):

$$HNR^2R^3 \quad (III)$$

in the presence of a basic compound,
wherein:
A is a covalent bond or a linear or branched divalent alkylene group comprising a number of carbon atoms ranging from 1 to 12,
$R^1$ is an optionally substituted hydrocarbon group, comprising from 1 to 36 carbon atoms,
$R^2$ and $R^3$, either identical or different, are optionally substituted alkyl groups, comprising from 1 to 36 carbon atoms, and
$R^2$ and $R^3$ not being simultaneously hydrogen atoms,
characterized by the fact that
the amine (III) is solubilized in an organic solvent, or in the diester compound (II),
when the amine (III) is solubilized in an organic solvent, the diester compound (II) is added onto the reaction mixture comprising the amine (III) and the basic compound,
when the amine (III) is solubilized in the diester compound (II), the basic compound is added onto the reaction mixture comprising the amine (III) and the diester compound (II),
the reaction is conducted at a temperature greater than or equal to 30° C.,
the amine (III) is present in molar excess ranging from 0.01 to 50%, based on the diester compound (II).

2. The method according to claim 1, wherein A is a branched divalent alkylene group, comprising a number of carbon atoms ranging from 2 to 12 carbon atoms.

3. The method according to claim 1, wherein the groups $R^1$, either identical or different, are hydrocarbon groups, comprising from 1 to 16 carbon atoms, which may bear one or several substituents.

4. The method according to claim 1, wherein the groups $R^1$, either identical or different, are selected from alkyl, alkenyl, cycloalkyl, aryl and arylalkyl groups, said groups bearing possibly one or several substituents.

5. The method according to claim 1, wherein $R^1$ is selected from methyl, ethyl, n-propyl, isopropyl, n-butyl, isobutyl, tertiobutyl, sec-butyl, n-pentyl, isopentyl, sec-pentyl, cyclopentyl, n-hexyl, isohexyl, sec-hexyl, cyclohexyl, methylcyclohexyl, 2-ethylbutyl, 3-methylpentyl, n-heptyl, isoheptyl, sec-heptyl, 3-methylhexyl, 4-methylhexyl, 1-ethylpentyl, 2-ethylpentyl, 3-ethylpentyl, n-octyl, isooctyl, 3-methylheptyl, n-nonyl, n-decyl, undecyl, n-dodecyl, tridecyl, tetradecyl and pentadecyl groups.

6. The method according to claim 1, wherein the diester compound of formula (II) is a mixture of diester compounds of the following formulae (II.1), (II.2) and (II.3):

$$R^1OOC-CH(CH_3)-CH_2-CH_2-COOR^1 \quad (II.1)$$

$$R^1OOC-CH(CH_2-CH_3)-CH_2-COOR^1 \quad (II.2)$$

$$R^1OOC-CH_2-CH_2-CH_2-CH_2-COOR^1 \quad (II.3)$$

7. The method according to claim 6, wherein the mixture of diester compounds of formulae (II.1), (II.2) and (II.3), has the following composition:

from 75 to 95% by weight of compound of formula (II.1),
from 3 to 23% by weight of compound of formula (II.2),
from 0.1 to 10% by weight of compound of formula (II.3).

8. The method according to claim 6, wherein the groups $R^1$ are methyl groups.

9. The method according to claim 1, wherein $R^2$ and $R^3$, either identical or different, are selected from methyl, ethyl, hydroxyethyl, n-propyl, isopropyl, n-butyl, isobutyl, tertiobutyl, n-pentyl, and hexyl groups.

10. The method according to claim 1, wherein the amine of formula (III) is solubilized in an organic solvent.

11. The method according to claim 10, wherein the organic solvent is selected from alcohols and ethers.

12. The method according to claim 1, wherein the basic compound is an alkaline or earth alkaline metal alkoxide.

13. The method according to claim 1, wherein the basic compound is introduced at a molar concentration relatively to the diester comprised between 0.01 and 20%.

14. The method according to claim 1, wherein the reaction is conducted at a temperature comprised between 30° C. and 130° C.

* * * * *